(12) United States Patent
Dror et al.

(10) Patent No.: US 8,568,773 B2
(45) Date of Patent: Oct. 29, 2013

(54) GLYCEROPHOSPHOLIPIDS FOR THE IMPROVEMENT OF COGNITIVE FUNCTIONS

(75) Inventors: Gai Ben Dror, Moshav Ofer (IL); Dorit Platt, Shimshit (IL); Orly Farkash, Shimshit (IL); Rassan Zuabi, Kfar Neen (IL); Zohar Bar-On, Karmiel (IL); Avidor Shulman, Kiryat Tivon (IL); Dori Pelled, Hod Hasharon (IL); Yael Richter, Moshav Beit Shearim (IL)

(73) Assignee: Enzymotec Ltd., Migdal HaEmeq (IL)

( * ) Notice: Subject to any disclaimer, the term of this patent is extended or adjusted under 35 U.S.C. 154(b) by 188 days.

(21) Appl. No.: 12/934,338

(22) PCT Filed: Jun. 24, 2009

(86) PCT No.: PCT/IL2009/000626
§ 371 (c)(1),
(2), (4) Date: Feb. 24, 2011

(87) PCT Pub. No.: WO2009/156991
PCT Pub. Date: Dec. 30, 2009

(65) Prior Publication Data
US 2011/0144063 A1    Jun. 16, 2011

(51) Int. Cl.
*A61K 31/66* (2006.01)
*A61K 9/64* (2006.01)
*A61K 47/00* (2006.01)
*A01N 57/00* (2006.01)

(52) U.S. Cl.
USPC ............ 424/456; 424/439; 514/114; 514/120

(58) Field of Classification Search
USPC ........................... 424/456, 429; 514/114, 120
See application file for complete search history.

(56) References Cited

U.S. PATENT DOCUMENTS

2009/0074857 A1    3/2009  Dror et al.

FOREIGN PATENT DOCUMENTS

| EP | 0 819 760 A1 | 1/1998 |
| WO | WO 2005/038037 A2 | 4/2005 |

OTHER PUBLICATIONS

International Search Report mailed by the International Searching Authority (ISA/EP) on Mar. 25, 2010 in connection with PCT International Application No. PCT/IL2009/000626, filed Jun. 24, 2009.
Written Opinion of the International Searching Authority mailed by the International Searching Authority (ISA/EP) on Mar. 25, 2010 in connection with PCT International Application No. PCT/IL2009/000626, filed Jun. 24, 2009.
International Preliminary Report on Patentability (Chapter I of the Patent Cooperation Treaty), including the Written Opinion of the International Searching Authority, issued by the International Bureau of WIPO on Jan. 5, 2011 in connection with PCT International Application No. PCT/IL2009/000626, filed Jun. 24, 2009.

*Primary Examiner* — Aradhana Sasan
(74) *Attorney, Agent, or Firm* — John P. White; Cooper & Dunham LLP

(57) ABSTRACT

The invention described herein provides a preparation comprising a non-mammalian derived mixture of serine glycerophospholipid conjugates with a specific content and specific conjugation patterns of LA, linolenic acid (alpha-linolenic acid, gamma-linolenic acid) DHA and EPA which depend on utilizing different sources of lipids, and uses of such preparations.

11 Claims, 1 Drawing Sheet

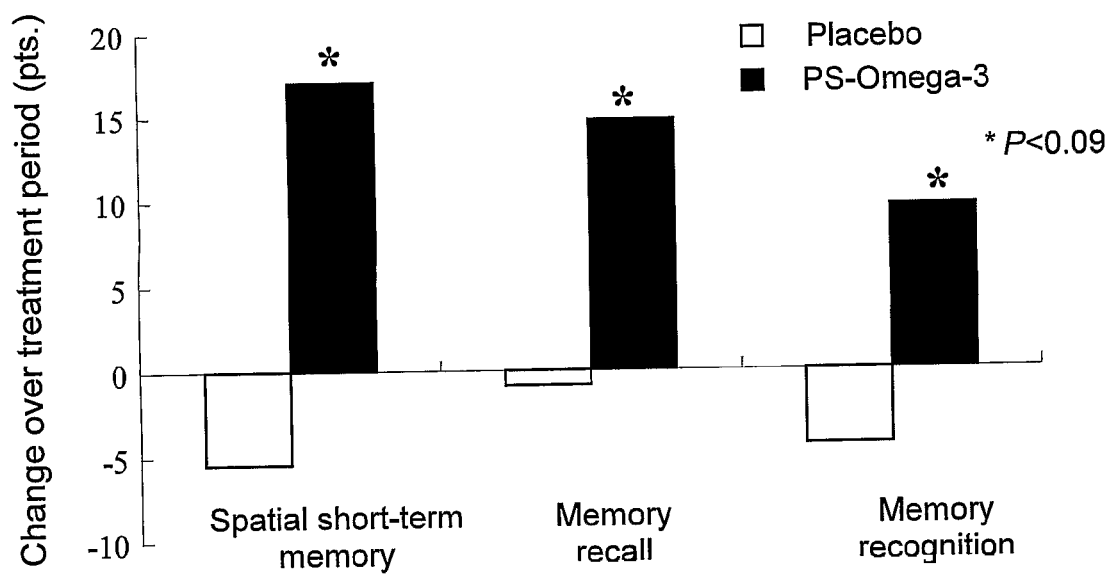

GLYCEROPHOSPHOLIPIDS FOR THE IMPROVEMENT OF COGNITIVE FUNCTIONS

CROSS REFERENCE TO RELATED APPLICATIONS

This application is a §371 national stage of PCT International Application No. PCT/IL2009/000626, filed Jun. 24, 2009, and PCT International Application No. PCT/IL2009/000626 claims priority of U.S. patent application Ser. No. 12/215,080, filed Jun. 24, 2008, the contents of which are hereby incorporated by reference into this application.

FIELD OF THE INVENTION

The present invention relates to serine glycerophospholipid preparations and their use in the improvement of cognitive functions.

BACKGROUND OF THE INVENTION

Glycerophospholipids, also referred to as phospholipids, are ubiquitous in nature, are key components of the lipid bilayer of cells, and are involved in cell metabolism and signaling. The hydroxyl groups of the glycerol backbone of phospholipids are substituted by a hydrophilic phosphate head and hydrophobic tail composed of non-polar fatty acids. Glycerophospholipids may be subdivided into distinct classes, based on the nature of the polar headgroup such as for example: phosphatidylcholine (also known as PC or lecithin), phosphatidylethanolamine (PE) and phosphatidylserine (PS). In addition to serving as a primary component of cellular membranes and binding sites for intra- and intercellular proteins, some glycerophospholipids, such as phosphatidylinositols and phosphatidic acids are either precursors of, or are themselves, membrane-derived second messengers. Animal studies have shown that PS enhances neuronal membrane function and hence slows cognitive decline, especially in the elderly [McDaniel M A et al. *Nutrition* 19: 957-75 (2003) and Jorissen B L et al. *Nutr Neurosci.* 4(2):121-34 (2001)].

Many health benefits have been attributed to the consumption of certain fatty acids. For example, polyunsaturated fatty acids (PUFA) of the type omega-3 and omega-6, have several health benefits on cardiovascular disease, immune disorders and inflammation, renal disorders, allergies, diabetes, and cancer. Extensive clinical studies investigating the importance of omega-3 fatty acids such as Docosahexaenoic acid (DHA) in the brain, found that low levels of DHA are associated with depression, memory loss, dementia, and visual problems. Studies showed an improvement in the elderly brain function as blood levels of DHA increased. Furthermore, DHA may have importance in the field of brain function enhancement, baby formula fortification, diabetics and cancer.

The human body does not adequately synthesize DHA. Therefore it is necessary to obtain it from the diet. Humans obtain DHA from their diets, initially through the placenta, then from breast milk, and later through dietary sources, such as fish, red meat, animal organ meat and eggs.

Linoleic acid (LA, C18:2, ω-6) and α-linolenic acid (ALA, C18:3, ω-3), are classified as essential fatty acids (EFA). The body cannot synthesize them de novo, and they must therefore be obtained through food sources providing them "ready-made". Both LA and ALA are needed for optimal growth and good health. Both LA and ALA are precursors of the ω-3 and ω-6 PUFA. LA is required for the synthesis of arachidonic acid (AA) (C20:4, ω-6), a key intermediate in the synthesis of eicosanoids, whereas ALA is used partly as a source of energy, and partly as a precursor for metabolites and longer chain PUFA. Within the human body LA and ALA can be elongated and desaturated to other more unsaturated fatty acids, principally AA and DHA (C22:6, ω-3), respectively.

Soybeans, egg yolk, bovine brain and fish are the major natural sources for obtaining and producing phospholipids, especially PS. The type of fatty acyl residues at the sn-1 and sn-2 positions in natural phospholipids vary, and their proportion in general depends on their source. For example, soybean is rich with LA fatty acid (about 54%) whereas fish derived lecithin is abundant with DHA fatty acid residue. The PS extracted from animal brain tissues, similar to human brain PS, has a fatty acid content which is characterized by relatively high levels of omega-3 moieties, compared to the levels of omega-3 found in plants, such as soy phospholipids. The bio-functionality of soybean PS in the improvement of cognitive function has been shown to be different from that of human brain PS [WO 2005/037848].

SUMMARY OF THE INVENTION

The present invention provides alternative, enhanced, and cheaper methods of improving cognitive functions in a subject using a lipid preparation conjugated with omega-3 and omega-6 fatty acids, with specific amounts and specific conjugation patterns of LA, linolenic acid (alpha-linolenic acid, gamma-linolenic acid), DHA and eicosapentaenoyl (EPA), e.g. utilizing different sources of lipids.

The subject invention thus provides a preparation comprising a non-mammalian derived mixture of serine glycerophospholipid conjugates wherein the mixture comprises (a) linoleic acid (C18:2) conjugated to PS and (b) DHA conjugated to PS wherein the w/w % of (a)/the w/w % of (b) is from about 0.09 to about 3.6.

In another one of its aspects the invention provides a method of improving a condition in a subject suffering from a cognitive disease or disorder comprising administering to a subject in need thereof a preparation of the invention.

In a further aspect the invention provides a use of a preparation of the invention for the manufacture of a nutritional, pharmaceutical or nutraceutical composition or a functional food.

In another aspect the invention provides a preparation of the invention for use in a nutritional, pharmaceutical or nutraceutical composition or a functional food.

The invention further provides a nutritional, pharmaceutical or nutraceutical composition or a functional food comprising a preparation of the invention.

In another one of its aspects the invention provides a preparation of the invention for use in improving a condition in a subject suffering from a cognitive disease or disorder.

BRIEF DESCRIPTION OF THE FIGURE

FIG. 1: shows a diagram depicting the spatial short-term memory, memory recall and memory recognition in adults upon administration of lipid preparation A of the invention in comparison to administration of placebo.

DETAILED DESCRIPTION OF THE INVENTION

In the first aspect of the present invention there is provided a preparation comprising a non-mammalian derived mixture of serine glycerophospholipid conjugates wherein the mixture comprises (a) linoleic acid (C18:2) conjugated to PS and (b) DHA conjugated to PS wherein the w/w % of (a)/the w/w % of (b) is from about 0.09 to about 3.6.

As used herein, the term "lipid" as used herein should be understood to encompass fats and fatlike compounds, which are essentially insoluble in water and which include, but are not limited to, triglycerides, sterols, fatty acids, and so forth.

As used herein the terms "glycerophospholipid" and "phospholipids" used interchangeably, should be understood to encompass a lipid of the general formula:

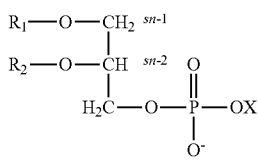

wherein the substituents, $R_1$ (substituent on position sn-1) and $R_2$ (substituent on position sn-2), are independent of each other and are selected from H or an acyl group selected from saturated, mono-unsaturated and polyunsaturated fatty acids. When X is serine, i.e. —$CH_2CH(COOH)NH_2$, the phospholipid is referred to as serine glycerophospholipid (PS).

The sn-1 and sn-2 positions as used herein and as indicated in above formula, refer to the respective carbon atoms on the glycerol backbone wherein $R_1$ and $R_2$, are substituted on the corresponding acyl groups.

In the present invention, the terms "substituted" and its lingual equivalents and the term "conjugated" and its lingual equivalents are interchangeably used and should be understood to encompass a fatty acid acyl covalently attached to the glycerophospholipid backbone of a serine glycerophospholipid of the invention. As noted above, the fatty acid may be attached to the sn-1 and/or sn-2 positions.

As used herein, the term "fatty acid" should be understood to encompass a carboxylic acid with a long unbranched aliphatic tail (chain), which is either saturated or unsaturated having one unsaturated bond (mono-unsaturated fatty acids) or two or more unsaturated bonds (poly-unsaturated fatty acids). When referring to a "fatty acid acyl" it should be understood to encompass an —C(=O)—R radical wherein R is a long unbranched aliphatic tail, which is either saturated or unsaturated having one unsaturated bond (mono-unsaturated fatty acids) or two or more unsaturated bonds (poly-unsaturated fatty acids).

Non-limiting examples of saturated fatty acids include: Butyric acid (Butanoic acid, C4:0), Caproic acid (Hexanoic acid, C6:0), Caprylic acid (Octanoic acid, C8:0), Capric acid (Decanoic acid, C10:0), Lauric acid (Dodecanoic acid, C12:0), Myristic acid (Tetradecanoic acid, C14:0), Palmitic acid (Hexadecanoic acid, C16:0), Stearic acid (Octadecanoic acid, C18:0), Arachidic acid (Eicosanoic acid, C20:0), Behenic acid (Docosanoic acid C22:0).

Non-limiting examples of unsaturated fatty acids include: Myristoleic acid (C14:1, ω-5), Palmitoleic acid (C16:1, ω-7), Oleic acid (C18:1, ω-9), Linoleic acid (C18:2, ω-6), Linolenic acid (C18:3) [Alpha-linolenic acid (C18:3, ω-3), Gamma-linolenic acid (C18:3, ω-6)], Eicosenoic acid (C20:1, ω-9), Arachidonic acid (C20:4, ω-6), Eicosapentaenoic acid (C20:5, ω-3), Erucic acid (C22:1, ω-9), Docosapentanoic acid (C22:5, ω-3) and Docosahexaenoic acid (C22:6, ω-3), Nervonic acid (C24:1, ω-9).

When referring to a "... [fatty acid] conjugated to PS ...", it should be understood to encompass a PS wherein a fatty acid acyl is conjugated at position sn-1 and/or position sn-2 of the phospholipid backbone (through the glycerol oxygen atom). In one embodiment a fatty acid is conjugated at position sn-1, and position sn-2 is either unsubstituted (e.g. having a hydrogen atom on the glycerol oxygen) or substituted with an acyl group selected from saturated, mono-unsaturated and polyunsaturated fatty acids, which may be the same or different from the substitution on position sn-1. In another embodiment a fatty acid is conjugated at position sn-2 and position sn-1 is either unsubstituted (e.g. having a hydrogen atom on the glycerol oxygen) or substituted with an acyl group selected from saturated, mono-unsaturated and polyunsaturated fatty acids, which may be the same or different from the substitution on position sn-2.

A preparation of the invention typically comprises a mixture of two or more serine glycerophospholipid conjugates of the invention, having fatty acid conjugation patterns as disclosed herein.

When referring to a w/w % of a fatty acid conjugated to PS in a preparation of the invention, it should be understood that the w/w % of said fatty acid which is conjugated to PS is calculated relative to the weight of the total fatty acids conjugated to PS in the preparation.

In one embodiment, the mixture of serine glycerophospholipid conjugates constitutes at least 10% w/w of the preparation. In another embodiment the mixture of serine glycerophospholipid conjugates constitutes at least 20% w/w of the preparation. In a further embodiment the mixture of serine glycerophospholipid conjugates constitutes at least 40% w/w of the preparation. In yet another embodiment the mixture of serine glycerophospholipid conjugates constitutes at least 50% w/w of the preparation. In a further embodiment the mixture of serine glycerophospholipid conjugates constitutes at least 54% w/w of the preparation.

It should be noted that the preparation of the invention may also comprise other phospholipids, such as phosphatidylcholine (PC), phosphatidylethanolamine (PE), phosphatidylinositol (PI), phosphatidylglycerol (PG) and phosphatidic acid (PA), to which fatty acid acyls are covalently attached (bonded) at either or both of the sn-1 or sn-2 positions of the glycerol moiety of the phospholipid. The fatty acid conjugation profile of any of the above-noted polar lipids may be the same as, or different from, the fatty acid conjugation profile of PS, as disclosed herein.

The terms "[PS] fatty acid conjugation pattern" and "[PS] fatty acid conjugation profile" are interchangeably used herein and refer to a particular content of specific fatty acids conjugated to PS and their position of substitution on the PS glycerol backbone.

In one embodiment, a preparation of the invention further comprises (c) linolenic acid (C18:3) conjugated to PS and (d) DHA conjugated to PS wherein the w/w % of (c)/w/w % of (d) is from about 0.01 to about 0.3.

In another embodiment, a preparation of the invention further comprises (e) linoleic acid (C18:2) conjugated to PS and (f) EPA conjugated to PS wherein the w/w % of (e)/w/w % of (f) is from about 0.23 to about 9.4.

In a further embodiment, a preparation of the invention further comprises (g) linolenic acid (C18:3) conjugated to PS and (h) EPA conjugated to PS wherein the w/w % of (g)/w/w % of (h) is from about 0.02 to about 0.8.

The preparation of the present invention may be prepared through enzymatic, chemical or molecular biology methods. Briefly, PS can be enriched with omega-3 or omega-6 fatty acids by enzymatic processes, e.g. enrichment of a natural phospholipid/lecithin with omega-3/omega-6 fatty acids by enzymatic transesterification/esterification followed by transformation of the head group to serine (using PLD enzymes) to obtain a PS-omega-3/omega-6 conjugate. Another enzymatic pathway is to obtain a phospholipid source which is naturally rich in omega-3 acids, such as marine-derived lecithin (e.g. hill, fish or algae) or eggs phospholipids, and transform their head groups to serine. It is to be noted that the fatty acid content of the PS obtained by this method has an omega-3 content which is predetermined by the source of choice (fish, krill, algae, soy etc.). Such methods have been described in WO 2005/038037.

The PS preparation of the present invention can also be prepared by chemical transesterification/esterification methods that will enrich the sn-1 and 2 positions with omega-3 or omega-6 acyl residues. Such methods of preparation of PS-omega-3 and PS-omega-6 have been described in WO 2005/038037.

Alternatively, the PS preparation of the present invention can be prepared by GMO (genetically modified. organisms)/biotechnology methods, for example, providing phospholipids-producing organisms with omega-3 or omega-6 fatty acids to obtain phospholipids enriched with omega-3 or omega-6 PS. It may be preferred to use genetically engineered plants or microorganisms, to avoid use of animal sources.

Thus, a mixture of serine glycerophospholipid conjugates of the invention is prepared from a natural, synthetic or semi-synthetic source or any combinations thereof. In an embodiment of the present invention, said natural source is derived from any one of plant (such as for example soy and algae), non-mammalian animal (such as for example krill, fish (such as for example Herring and blue Whiting)), or microorganism (such as for example bacteria) source or any combinations thereof. PS from different sources have different fatty acid conjugation patterns. For example, soy lecithin contains higher levels of linoleic acid conjugated to PS as compared with marine lecithin which contains higher levels of DHA conjugated to PS.

In yet a further embodiment, the production of said lipid preparation involves an enzymatic catalysis.

PS extracted from bovine cortex (BC-PS) is associated with a positive effect on brain function and cognitive abilities, while PS derived from soybean (SB-PS) obtained inconclusive results regarding its ability to improve cognitive functions. Without being bound by theory, this difference in efficacy was attributed to the different fatty acid composition of the two PS sources. While BC-PS has a relatively high DHA content and low LA content, SB-PS is enriched with LA and has no DHA attached to its backbone. It is thus assumed that the PS compositions with low ratio of LA/DHA will serve as better cognitive enhancers.

The present invention surprisingly provides specific preparations of PS with LA/DHA ratios of 0.09-3.6 which are as effective, and in some cases even more effective, than PS preparations with lower LA/DHA ratios (more DHA), in their ability to enhance cognitive functions.

The subject invention envisages that the use of a preparation of the invention comprising a mixture of serine glycerophospholipids with specific fatty acid conjugation patterns, which may be derived from distinct sources or may be prepared synthetically, results in similar or improved cognitive functions as compared to lipid preparations derived from a single source or prepared to mimic the fatty acid content of a lipid preparation derived from a single source. For example, a lipid preparation comprising PS conjugated with more LA than purely marine-derived lipid preparations, have a similar or improved effect on cognitive functions as compared to either plant derived (such as soy) lipids on the one hand or marine derived (such as fish) lipids on the other. Such lipid preparations, derived from more than one source or prepared synthetically to mimic the fatty acid content of lipid preparations derived from more than one source, are also cheaper to prepare than purely marine derived lipid preparations.

The preparation of the invention may be in the form of fluid oil, powder, granules, wax, paste, oil or aqueous emulsion, and any other form that will enable its use in the target applications.

In another one of its aspects the invention provides a use of a preparation of the invention, for the manufacture of a nutritional, pharmaceutical or nutraceutical composition or a functional food.

In a further aspect the invention provides a preparation of the invention, for use in a nutritional, pharmaceutical or nutraceutical composition or a functional food.

In yet a further aspect the invention provides a nutritional, pharmaceutical or nutraceutical composition or a functional food comprising a preparation of the invention.

A nutritional composition as used herein can be any nutritional composition including, but not limited to, human milk fat substitute, infant formula, dairy product, milk powder, drinks, ice-cream, biscuit, soy product, bakery, pastry and bread, sauce, soup, prepared food, frozen food, condiment, confectionary, oils and fat, margarine, spread, filling, cereal, instant product, infant food, toddler food, bar, snack, candy and chocolate product.

The term "infant formula" as used herein encompasses infant formulas (for newborn to 6 months old infants), follow-up formulas (for 6-12 months old babies) and growing up formulas (for 1-3 years old children).

A functional food as used herein can be any functional food, including, but not limited to, dairy product, ice-cream, biscuit, soy product, bakery, pastry, cakes and bread, instant product, sauce, soup, prepared food, frozen food, condiment, confectionary, oils and fat, margarine, spread, filling, cereal, instant product, drinks and shake, infant food, bar, snack, candy and chocolate product.

A nutraceutical composition as used herein can be any nutraceutical, which can be any substance that may be considered a food or part of a food and provides medical or health benefits, including the prevention and treatment of diseases or disorders. Such nutraceutical compositions include, but are not limited to, a food additive, a food supplement, a dietary supplement, genetically engineered foods such as for example vegetables, herbal products, and processed foods such as cereals, soups and beverages and stimulant functional food, medical food and pharmafood. Dietary supplements may be delivered in the form of soft gel capsules, tablets, syrups, and other known dietary supplement delivery systems.

In an embodiment of the invention, the pharmaceutical or nutraceutical compositions are in a dosage delivery form.

Suitable routes of administration for the compositions of the subject invention are oral, buccal, sublingual administration, administration via a feeding tube, topical, transdermal, or parenteral (including subcutaneous, intramuscular, intravenous and intradermal) administration. In one embodiment, the compounds are administered orally.

The exact dose and regimen of administration of the composition will necessarily be dependent upon the therapeutic effect to be achieved (e.g. improving a condition in a subject suffering from a cognitive disease or disorder) and may vary with the particular formula, the route of administration, and the age and condition of the individual subject to whom the composition is to be administered.

The present invention thus also provides pharmaceutical compositions of the invention in admixture with (pharmaceutically) acceptable auxiliaries, and optionally other therapeutic agents. The auxiliaries must be "acceptable" in the sense of being compatible with the other ingredients of the composition and not deleterious to the recipients thereof.

In one embodiment, a pharmaceutical composition of the invention further comprises at least one pharmaceutically active agent.

The pharmaceutical and nutraceutical compositions may be prepared by any method well known in the art of pharmacy. Such methods include the step of bringing in association the ingredients with any auxiliary agent. The auxiliary agent(s), also named accessory ingredient(s), include those conventional in the art, such as carriers, fillers, binders, diluents, dessicants, disintegrants, lubricants, colorants, flavoring agents, anti-oxidants, and wetting agents.

The pharmaceutical and nutraceutical compositions of the invention may further comprise edible fibers, aroma, taste ingredients, and ingredients that control physical and organoleptic properties.

Pharmaceutical compositions suitable for oral administration may be presented as discrete dosage units such as pills, tablets, pellets, dragees, or capsules, or as a powder or granules, or as a solution, suspension or elixir.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated.

The compositions may be presented in unit-dose or multi-dose containers, for example sealed vials and ampoules, and may be stored in a freeze-dried (lyophilised) condition requiring only the addition of sterile liquid carrier, for example water, prior to use.

The invention further provides a commercial package and/or kit for preparing a composition of the invention such as an edible fat source or food article in accordance with the invention comprising (a) a fat source; (b) optionally at least one of edible physiologically acceptable protein, carbohydrate, vitamin, mineral, amino acid, nucleotide and active or non-active additive; (c) optionally at least one edible physiologically acceptable carrier or diluent for carrying the constituent/s defined in (a) and (b); (d) means and receptacles for admixing the constituents defined in (a), (b) and/or (c); and (e) instructions for use such as, but not limited to terms of storage, instructions for preparation of the fat source or food article for administration, required dilutions, dosages, frequency of administration and the like.

A commercial package or kit in accordance with the invention may also contain a fat source of the invention in a ready-to-use form, together with instructions for use. Dosages are usually determined according to age, weight, sex and condition of the subject, in accordance with good medical practice known to the attending physician and other medical personnel.

In another one of its aspects the invention provides a method of improving a condition in a subject suffering from a cognitive disease or disorder comprising administering to a subject in need thereof a preparation of the invention.

The invention further provides a use of a preparation of the invention for the manufacture of a nutritional, pharmaceutical or nutraceutical composition or a functional food for improving a condition in a subject suffering from a cognitive disease or disorder.

In another one of its aspects the invention provides a preparation of the invention for use in improving a condition in a subject suffering from a cognitive disease or disorder.

The term "cognitive disease or disorder" as used herein should be understood to encompass any cognitive disease or disorder. Non-limiting examples of such a cognitive disease or disorder are Attention Deficit Disorder (ADD), Attention Deficit Hyperactivity Disorder (ADHD), dyslexia, age-associated memory impairment and learning disorders, amnesia, mild cognitive impairment, cognitively impaired non-demented, pre-Alzheimer's disease, Alzheimer's disease, Parkinson's disease, pre-dementia syndrome, dementia, age related cognitive decline, cognitive deterioration, moderate mental impairment, mental deterioration as a result of aging, conditions that influence the intensity of brain waves and/or brain glucose utilization, stress, anxiety, depression, behavior disorders, concentration and attention impairment, mood deterioration, general cognitive and mental well being, neurodegenerative disorders, hormonal disorders or any combinations thereof. In a specific embodiment, the cognitive disorder is memory impairment.

The term "improving a condition in a subject suffering from a cognitive disease or a cognitive disorder" as used herein should be understood to encompass: ameliorating undesired symptoms associated with a disease, disorder, or pathological condition; preventing manifestation of symptoms before they occur; slowing down progression of a disease or disorder; slowing down deterioration of a disease or disorder; slowing down irreversible damage caused in a progressive (or chronic) stage of a disease or disorder; delaying onset of a (progressive) disease or disorder; reducing severity of a disease or disorder; curing a disease or disorder; preventing a disease or disorder from occurring altogether (for example in an individual generally prone to the disease) or a combination of any of the above. For example, in a subject suffering from memory impairment, for example as a result of Alzheimer's Disease, symptoms including deterioration of spatial short-term memory, memory recall and/or memory recognition, focused and sustained attention, learning, executive functions and/or mental flexibility are improved by use of a lipid preparation of the invention.

In one embodiment of the invention a cognitive disease or disorder is selected from the group consisting of Attention Deficit Disorder, Attention Deficit Hyperactivity Disorder, dyslexia, age-associated memory impairment and learning disorders, amnesia, mild cognitive impairment, cognitively impaired non-demented, pre-Alzheimer's disease, Alzheimer's disease, Parkinson' disease, pre-dementia syndrome, dementia, age related cognitive decline, cognitive deterioration, moderate mental impairment, mental deterioration due to aging, conditions that influence the intensity of brain waves and/or brain glucose utilization, stress, anxiety, depression, behavior disorders, concentration and attention impairment, mood deterioration, general cognitive and mental well being, neurodegenerative disorders, hormonal disorders and any combinations thereof.

It will be appreciated that a composition (whether pharmaceutical, nutraceutical, nutritional, etc) or product (e.g. functional food) of the invention may be combined with other treatment methods known in the art (i.e., combination therapy). Thus, treatment of cognitive diseases or disorders using a composition or product of the invention may be combined with conventional drugs for the treatment of cognitive diseases or disorders.

Non limiting examples of drugs indicated for the treatment of cognitive diseases or disorders include Acetylcholine esterase inhibitors (such as for example aricept (donepezil), exelon (rivastigmine), reminyl (galantamine), N-methyl-D-aspartate (NMDA) receptor antagonists (such as for example AP5 (APV, R-2-amino-5-phosphonopentanoate), AP7 (2-amino-7-phosphonoheptanoic acid), CPPene (3-[(R)-2-carboxypiperazin-4-yl]-prop-2-enyl-1-phosphonic acid), Amantadine: Dextromethorphan, Dextrorphan, Ibogaine, Ketamine, Memantine, Nitrous oxide, Phencyclidine, Riluzole, Tiletamine, Aptiganel, HU-211, HU-210, Remacimide, 1-Aminocyclopropanecarboxylic acid, DCKA (5,7-dichlorokynurenic acid), Kynurenic acid, and Lacosamide.

A composition or product of the invention may also be administered in conjunction with other compounds, including, but not limited to folic acid, vitamins, minerals, amino acids, nucleotides, antioxidants and so forth.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Example 1

Method of Preparing a Lipid Preparation of the Invention

Lipid preparations A, A1, A2, C, D, F, G, H, I, J, K, L, M, and N are prepared as follows:

Marine lecithin produced by an extraction process from biomass derived from fish (mainly Herring and blue Whiting) was dissolved in organic solvents and allowed to react with an aqueous solution containing L-serine, $CaCl_2$, phospholipase D (PLD) and acetate buffer at pH of 5.6. The resulting PS preparation was purified by removal of the water phase, evaporation of the organic solvents and further purification stages. The resulted powder contained 44% PS and 31% DHA from PS fatty acids.

PC enriched soybean lecithin was reacted with aqueous medium containing L-serine, $CaCl_2$, PLD and acetate buffer at pH of 5.6. The resulting PS preparation was washed from water soluble material (salts, serine etc.) and further purified. The resulting powder contained 67.4% PS.

The powder obtained from the marine lecithin origin, and the powder obtained from the soybean lecithin origin, were mixed together in ratios as described in Table 5.

Alternatively, lipid preparations A, A1, A2, C, D, F, G, H, I, J, K, L, M, and N are prepared as follows:

120 gram of marine lecithin and 60 gram PC enriched soybean lecithin are dissolved together in organic solvents in a 3 liter glass lab reactor. The described organic phase is allowed to react with an aqueous solution containing L-serine, $CaCl_2$, PLD and acetate buffer at pH of 5.6. The resulted PS is purified by removal of the water phase, evaporation of the organic solvents and further purification stages.

Lipid Preparation B was Prepared as Follows:

Marine lecithin produced by an extraction process from biomass derived from fish (mainly Herring and blue Whiting) was dissolved in organic solvents and allowed to react with an aqueous solution containing L-serine, $CaCl_2$, phospholipase D (PLD) and acetate buffer at pH of 5.6. The resulting PS preparation was purified by removal of the water phase, evaporation of the organic solvents and further purification stages. The resulting powder contained 44% PS and 31% DHA from PS fatty acids.

Lipid Preparation E was Prepared as Follows:

PC enriched soybean lecithin was reacted to PS in aqueous medium that containing L-serine, $CaCl_2$, PLD and acetate buffer at pH of 5.6. The resulting PS was washed from water soluble material (salts, serine etc.) and further purified. The resulting powder contained 67% PS.

Table 5 provides the fatty acid ratio and the source ratio of preparations A, B, C, D, E and F of the examples below. The fatty acid and phospholipid content of each of these lipid preparations is further specified in Tables 2 and 3 below.

Lipid preparations A, A1 and A2 are different batches of the same preparation.

Lipid preparations A, A1 and A2 have a ratio between linoleic acid (C18:2) (LA) conjugated to PS (w/w %) and Docosahexaenoic acid (DHA) conjugated to PS (w/w %) of about 0.9-1.4; have a ratio between linolenic acid (18:3) conjugated to PS (w/w %) and DHA conjugated to PS (w/w %) of about 0.08-0.13; have a ratio between LA (18:2) conjugated to PS (w/w %) and EPA conjugated to PS (w/w %) of about 2.3-3.5; and have a ratio between linolenic acid (18:3) conjugated to PS (w/w %) and EPA conjugated to PS (w/w %) of about 0.2-0.3, wherein the total DHA conjugated to PS constitutes about 19-22% w/w of total fatty acids conjugated to PS.

Lipid preparation B (100% marine-derived) has a ratio between linoleic acid (LA) (C18:2) conjugated to PS (w/w %) and DHA conjugated to PS (w/w %) of at most about 0.02; has a ratio between Linolenic acid (18:3) conjugated to PS (w/w %) and DHA conjugated to PS (w/w %) of at most about 0.02; has a ratio between LA (18:2) conjugated to PS (w/w %) and EPA conjugated to PS (w/w %) of at most about 0.05; and has a ratio between linolenic acid (18:3) conjugated to PS (w/w %) and EPA conjugated to PS (w/w %) of at most about 0.05; wherein the total DHA conjugated to PS constitutes about 31% w/w of total fatty acids conjugated to PS.

Lipid preparation C has a ratio between linoleic acid (LA) (C18:2) conjugated to PS (w/w %) and DHA conjugated to PS (w/w %) of about 0.1; has a ratio between linolenic acid (18:3) conjugated to PS (w/w %) and DHA conjugated to PS (w/w %) of about 0.01; has a ratio between LA (18:2) conjugated to PS (w/w %) and EPA conjugated to PS (w/w %) of about 0.23; and has a ratio between Linolenic acid (18:3) conjugated to PS (w/w %) and EPA conjugated to PS (w/w %) of about 0.02; wherein the total DHA conjugated to PS constitutes about 30% w/w of total fatty acids conjugated to PS.

Lipid preparation D has a ratio between linoleic acid (LA) (C18:2) conjugated to PS (w/w %) and DHA conjugated to PS (w/w %) of about 3.6; has a ratio between Linolenic acid (18:3) conjugated to PS (w/w %) and DHA conjugated to PS (w/w %) of about 0.3; has a ratio between LA (18:2) conjugated to PS (w/w %) and EPA conjugated to PS (w/w %) of about 9.4; and has a ratio between Linolenic acid (18:3) conjugated to PS (w/w %) and DHA conjugated to PS (w/w %) of about 0.8; wherein the total DHA conjugated to PS constitutes about 11% w/w of total fatty acids conjugated to PS.

Lipid preparation E (100% soy-derived) has a ratio between linoleic acid (LA) (C18:2) conjugated to PS (w/w %) and DHA conjugated to PS (w/w %) of above 100; has a ratio between Linolenic acid (18:3) conjugated to PS (w/w %) and DHA conjugated to PS (w/w %) of above 10; has a ratio between LA (18:2) conjugated to PS (w/w %) and EPA conjugated to PS (w/w %) of above 100; and has a ratio between Linolenic acid (18:3) conjugated to PS (w/w %) and EPA conjugated to PS (w/w %) of above 10, with practically no DHA.

Lipid preparation F has a ratio between linoleic acid (LA) (C18:2) conjugated to PS (w/w %) and DHA conjugated to PS (w/w %) of about 9; has a ratio between Linolenic acid (18:3) conjugated to PS (w/w %)and DHA conjugated to PS (w/w %) of about 0.7; has a ratio between LA (18:2) conjugated to PS (w/w %) and EPA conjugated to PS (w/w %) of about 23; and has a ratio between Linolenic acid (18:3) conjugated to PS (w/w %) and DHA conjugated to PS (w/w %) of about 1.8; wherein the total DHA conjugated to PS constitutes about 5.6% w/w of total fatty acids conjugated to PS.

In order to avoid hyper-inflammatory situations, it is preferable to supplement subjects with omega-3 fatty acids in a balanced ratio with omega-6 fatty acids. Omega 3 fatty acids increase bleeding time, decrease platelet aggregation, blood viscosity, and fibrinogen; and increase erythrocyte deformability; thus decreasing the tendency to thrombus formation. Table 8 shows the ratio between omega 6 and omega 3 fatty acids conjugated to PS and shows that preparations A, C and D have balanced ratios whereas a ratio of <0.01 (as in preparation B) or >10 (as in preparation E) may be considered not balanced.

It is to be understood that the subject invention is not limited to preparations A, C and D. Other preparations (G-N) comprising for example 50%, 55%, 60%, 65%, 70%, 80%, 85%, and 90% marine material (i.e. 50%, 45%, 40%, 35%, 30%, 20%, 15%, and 10% soy material) are also envisaged (Table 9).

Example 2

Efficacy of Lipid Preparation A

I. The efficacy of lipid preparation A (prepared according to Example 1 above), was investigated in a single-center, double-blind, randomized, placebo-controlled ~3 months trial in elderly with impaired cognitive performance.

According to the study design, 160 subjects were intended to be randomized following screening to one of two treatment groups, 80 subjects in each treatment group:
(a) 1 capsule containing 200 mg of lipid preparation A, was administered three (3) times daily with meals.
(b) placebo—1 capsule containing 260-270 mg cellulose was administered three (3) times daily with meals.

The capsules containing lipid preparation A and the placebo capsules were of identical appearance, taste and smell.

Memory functions of 15 subjects who received preparation A treatment and 18 subjects who received placebo capsules were tested using NexAde computerized neuropsychological assessment software (NexSig Neurological Examination Technologies Ltd, Israel) at baseline and following ~3 treatment months.

The computerized neuropsychological assessment software consisted of seven separate tasks including: symbol spotting, pattern identification, pattern recall, digit-symbol substitution, digits span forward, digits span backward and delayed pattern recall. Based on the results obtained in the single tasks, eight cognitive composite scores were calculated including focused attention (the ability to respond discretely to specific visual auditory or tactile stimuli), sustained attention (the ability to maintain a consistent behavioral response during continuous and repetitive activity), memory recognition (the ability to identify previously stored information), memory recall (involves digging into the memory and bringing back information on a stimulus/response basis), visuospatial learning, spatial short term memory (a memory system that stores spatial information for a few seconds so that it can be used in the service of ongoing cognitive tasks), executive functions and mental flexibility. A final score which considered all of the cognitive composite scores was calculated as well. The software presented different, though equivalent, forms of the tests, which allowed repeated testing. All tasks were computer-controlled and no previous experience with computers or typing was required (Aharonson V, Korczyn A D: *Human computer interaction in the administration and analysis of neuropsychological tests*. elsevier science publishers B.V. 2004; 73:43-53).

Results

FIG. 1 indicates that lipid preparation A improved memory parameters following ~3 months treatment period.

FIG. 1 demonstrates three of the memory parameters that were tested: memory recall, memory recognition and spatial short term memory. Memory recall and recognition is a "process" used to get information back out of our memory. Memory recall involves digging into the memory and bringing back information on a stimulus/response basis, and memory recognition indicates the ability to identify previously stored information.

Spatial short term memory is a memory system that stores spatial information for a few seconds so that it can be used in the service of ongoing cognitive tasks. The results presented in FIG. 1 show that lipid preparation A improved cognitive performance of learning and memory abilities in comparison with placebo.

Thus, lipid preparation A improved mild cognitive impairment and age-associated memory impairment.

II. The efficacy of lipid preparation A (prepared according to Example 1 above), was further investigated in a single center, 3 months trial, in 52 elderly (age ≥60) with impaired cognitive performance.

Subjects received one capsule containing 200 mg of lipid preparation A (containing 100 mg PS) three times a day.

Memory functions of the subjects were tested at baseline and following 3 treatment months using the following test procedures:
1. NexAde™ computerized cognitive assessment tool (as described above).
2. Rey-Auditory Verbal Learning Test (AVLT) (Rey A: *L'Examen Clinique en Psychologie Paris: Press Universitaire de France* 1964)

This test consisted of a list of 15 common nouns, which were read to the subject in five consecutive trials (trials 1 through 5); each reading was followed by a free recall task. In trial 6, an interference list of 15 new common nouns was presented, followed by free recall of these new nouns. In trial 7, without additional reading, subjects were again asked to recall the first list. Twenty minutes later, and again without an additional reading, subjects were asked to recall again the first list (trial 8). Five different scores were derived from the test; immediate memory recall (trial 1 score), total immediate recall (sum of scores of trial 1 and 6), best learning (trial 5), verbal total learning (sum of scores of trial 1 through 5) and delayed memory recall (trial 8).

Results

Table 1 indicates that lipid preparation A significantly improved the final score of the computerized cognitive assessment tool. This score is an adjusted calculation that sums the different composite scores. Table 1 demonstrates individual tests (digits recall forward and backward) and specific composite scores (focused attention, memory recall and memory recognition) that were significantly improved. It is concluded that lipid composition A significantly improved numerous cognitive parameters such as attention, memory and learning.

TABLE 1

The effect of Lipid preparation A on the computerized cognitive assessment tool parameters

| Tested parameters | Mean change from baseline ± SE | p* |
|---|---|---|
| Digits recall forward | 5.44 ± 2.54 | 0.076 |
| Digits recall backward | 2.98 ± 2.38 | 0.001 |
| Focused attention | 3.81 ± 1.65 | 0.003 |
| Memory recognition | 8.29 ± 2.06 | 0.032 |
| Memory recall | 5.17 ± 1.46 | 0.025 |
| Final score | 5.12 ± 1.77 | 0.002 |

*Based on two-side students' T-test for dependent samples.

Table 2 indicates that lipid preparation A improved the different parameters of Rey-AVLT procedure, and thus further confirms the cognitive enhancement properties of the preparation. Specifically, lipid composition A significantly improved immediate and delayed memory recall, best learning, total learning and total immediate recall.

TABLE 2

Effect of lipid preparation A on Rey-AVLT parameters

| Tested parameters | Mean change from baseline ± SE | p* |
|---|---|---|
| Immediate memory recall | 1.87 ± 0.26 | <0.001 |
| Best learning | 0.65 ± 0.28 | <0.001 |
| Delayed memory recall | 1.10 ± 0.32 | <0.001 |
| Verbal total learning | 6.17 ± 0.94 | <0.001 |
| Total immediate recall | 2.19 ± 0.43 | <0.001 |

*Based on two-side students' T-test for dependent samples.

In conclusion, lipid preparation A improved mild cognitive impairment and age-associated memory impairment.

Example 3

Efficacy of Lipid Preparations B, C, D, E, and F

All trials described tested the same population (elderly subjects with impaired cognitive performance) and utilized the same cognitive assessment tools.

Efficacy of Lipid Preparation B

The efficacy of lipid preparation B (prepared according to Example 1 above) was investigated in a single-center, open label, ~3 months trial in 16 elderly (age≥60) with impaired cognitive performance.

1 capsule containing 227 mg of lipid preparation B (containing 100 mg PS) was administered three (3) times daily with meals.

Memory functions of the subjects were tested at baseline and following 3 treatment months using computerized cognitive assessment tool essentially as described in Example 2 above.

Results

Table 3 indicates that lipid preparation B improved the final score of the computerized cognitive assessment tool. Although the improvement did not reach statistical significance, its magnitude was comparable to that following lipid preparation A consumption (see Table 1). An improvement was also detected in individual tests (digits recall forward and backward) and specific composite scores (spatial short term memory, focused attention, memory recall and memory recognition) that were improved by lipid preparation B. Again, the magnitude of the effect was comparable to that following treatment with preparation A (see Table 1), but the improvement didn't always reach statistical significance. It is thus concluded that lipid preparation B improved several cognitive parameters similarly to lipid preparation A, however, since the improvement did not always reach statistical significance, it seems that lipid preparation A has an advantage over lipid preparation B in improving cognitive skills and treating mild cognitive impairment and age associated memory decline. These results are surprising since lipid preparation B has a lower LA/DHA ratio (more DHA) in comparison with lipid preparation A.

TABLE 3

Effect of lipid preparation B on the computerized cognitive assessment tool parameters

| Tested parameters | Mean change from baseline ± SE | p* |
|---|---|---|
| Digits recall forward | 4.63 ± 5.70 | 0.870 |
| Digits recall backward | 0.88 ± 4.94 | 0.987 |
| Focused attention | 3.25 ± 3.21 | 0.070 |
| Memory recognition | 2.75 ± 2.20 | 0.033 |
| Memory recall | 5.94 ± 2.79 | 0.032 |
| Final score | 5.05 ± 2.67 | 0.133 |

*Based on two-side students' T-test for dependent samples.

Efficacy of Lipid Preparation C

The efficacy of lipid preparation C is investigated in a single-center, open label, ~3 months trial in 8 elderly with impaired cognitive performance.

1 capsule containing 222 mg lipid preparation C (containing 100 mg PS) is administered three (3) times daily with meals.

Memory functions of the subjects are tested using computerized cognitive assessment tool and Rey-AVLT essentially as described in Example 2.

Results

Lipid preparation C improves memory recall, memory recognition, attention, concentration, learning and spatial short term memory following ~3 months treatment period. The improvement of all parameters tested is similar to the improvement following ~3 treatment months with lipid preparation A (Example 2) and similar to, or better than, the improvement following ~3 treatment months with lipid preparation B.

Efficacy of Lipid Preparation D

The efficacy of lipid preparation D is investigated in a single-center, open label, ~3 months trial in 8 elderly with impaired cognitive performance.

1 capsule containing 176 mg of lipid preparation D (containing 100 mg PS) is administered three (3) times daily with meals.

Memory functions of the subjects are tested using computerized cognitive assessment tool and Rey-AVLT essentially as described in Example 2.

Results

Lipid preparation D improves memory recall, memory recognition, attention, concentration, learning and spatial short term memory following ~3 months treatment period. The improvement of all parameters tested is similar to the improvement following ~3 treatment months with lipid preparation A (Example 2) and C, and similar to or better than the improvement following ~3 treatment months with lipid preparation B.

Efficacy of Lipid Preparation E

The efficacy of lipid preparation E (prepared according to Example 1 above) was investigated in a single-center, open label, ~3 months trial in 24 elderly (age≥60) with impaired cognitive performance.

1 capsule containing 150 mg of lipid preparation E (containing 100 mg PS) was administered three (3) times daily with meals.

Memory functions of the subjects were tested at baseline and following 3 treatment months using Rey-AVLT procedure essentially as described in Example 2.

Results

Table 4 indicates that lipid preparation E, as lipid preparation A, improved the parameters tested in Rey-AVLT procedure. However, in comparison with lipid preparation A, the magnitude of the effect was considerably smaller. Comparison between lipid preparation A and E revealed a statistical significant difference, in favor of preparation A, between the two treatments in immediate recall ($p=0.05$) and total immediate recall ($p=0.03$) and a trend in the total learning score ($p=0.13$). This difference reflects the superiority of lipid preparation A over lipid preparation E in the treatment of cognitive deterioration.

In addition, memory functions of the subjects are tested at baseline and following 3 treatment months using the computerized cognitive assessment tool essentially as described in Example 2.

Results

Lipid preparation E tends to improve memory recall, memory recognition, attention, concentration, learning and spatial short term memory only to a minor extent following ~3 months treatment period. The improvement of all parameters tested is lower than the improvement following ~3 treatment months with any of the lipid preparations A (Example 2), B, C and D.

Efficacy of Lipid Preparation F

The efficacy of lipid preparation is investigated in a single-center, open label, ~3 months trial in 8 elderly with impaired cognitive performance.

1 capsule containing 162 mg of lipid preparation F (containing 100 mg PS) is administered three (3) times daily with meals.

Memory functions of the subjects are tested using computerized cognitive assessment tool and Rey-AVLT procedure essentially as described in Example 2.

Results

Lipid preparation F tends to improve memory recall, memory recognition, attention, concentration, learning and spatial short term memory only to a minor extent following ~3 months treatment period. The improvement of all parameters tested is lower than the improvement following ~3 treatment months with any of the lipid preparations A (Example 2), B, C and D.

TABLE 5

Fatty acid content* and Source of Preparations A-F

| | w/w %* LA conjugated to PS/w/w % DHA conjugated to PS | w/w % Linolenic acid conjugated to PS/w/w % DHA conjugated to PS | w/w % LA conjugated to PS/w/w % EPA conjugated to PS | w/w % Linolenic acid conjugated to PS/w/w % EPA conjugated to PS | % Soy PS Source | % Marine PS Source |
|---|---|---|---|---|---|---|
| Preparation A | 1:1 | 0.08:1 | 2.5:1 | 0.2:1 | 25 | 75 |
| Preparation A1 | 0.94:1 | 0.09:1 | 2.36:1 | 0.23:1 | 25 | 75 |
| Preparation A2 | 1.38:1 | 0.13:1 | 3.46:1 | 0.32:1 | 25 | 75 |
| Preparation B | <0.02:1 | ≤0.02:1 | ≤0.05:1 | ≤0.05:1 | 0 | 100 |
| Preparation C | 0.09:1 | 0.01:1 | 0.23:1 | 0.02:1 | 3 | 97 |
| Preparation D | 3.6:1 | 0.3:1 | 9.4:1 | 0.8:1 | 55 | 45 |
| Preparation E | >100:1 | ≥10:1 | ≥100:1 | ≥10:1 | 100 | 0 |
| Preparation F | 8.9:1 | 0.7:1 | 23:1 | 1.8:1 | 75 | 25 |

*Weight percent of a fatty acid conjugated to PS relative to weight of the total fatty acids conjugated to PS

TABLE 4

Effect of lipid preparation E on Rey-AVLT parameters

| Tested parameters | Mean change from baseline ± SE | P* |
|---|---|---|
| Immediate memory recall | 0.96 ± 0.36 | 0.032 |
| Best learning | 0.42 ± 0.53 | 0.002 |
| Delayed memory recall | 0.71 ± 0.50 | <0.001 |
| Verbal total learning | 3.54 ± 1.47 | <0.001 |
| Total immediate recall | 0.58 ± 0.48 | 0.001 |

*Based on two-side students' T-test for dependent samples.

TABLE 6

Phospholipid content (w/w %) of Preparations A-F

| | PS | PC | PI | PE | PA |
|---|---|---|---|---|---|
| Preparation A | 50 | 0-1 | 0-3 | 3 | 8 |
| Preparation A1 | 54 | 0-1 | 0-3 | 3.5 | 9 |
| Preparation A2 | 54 | 0-1 | 0-3 | 3.5 | 9 |
| Preparation B | 44 | 0-1 | 0-3 | 4 | 7.5 |
| Preparation C | 45 | 0-1 | 0-3 | 4 | 8 |
| Preparation D | 57 | 0-1 | 0-3 | 2.5 | 9 |
| Preparation E | 67 | 0-1 | 0-3 | 1 | 11 |
| Preparation F | 62 | 0-1 | 0-3 | 2 | 10 |

TABLE 7

Fatty acid conjugated to PS (weight percent from total fatty acids conjugated to PS)

|  | C14 | C16 | C16:1 | C18 | C18:1 | C18:2 | C18:3 | C20:1 | C20:5 | C22:6 |
|---|---|---|---|---|---|---|---|---|---|---|
| Preparation A | 1.5 | 24.7 | 1.7 | 3.1 | 16.5 | 20.5 | 1.7 | 1.5 | 8.0 | 20.6 |
| Preparation A1 | 1.6 | 20.6 | 0.9 | 2.7 | 15.1 | 20.7 | 2.0 | 1.6 | 8.8 | 22.0 |
| Preparation A2 | 1.4 | 19.9 | 0.9 | 3.0 | 15.7 | 26.2 | 2.4 | 1.3 | 7.6 | 19.0 |
| Preparation B | 2.2 | 29.8 | 2.6 | 2.2 | 18.0 | ≤0.5 | ≤0.5 | 2.2 | 12.0 | 31.0 |
| Preparation C | 2.1 | 29.1 | 2.5 | 2.3 | 17.8 | 2.7 | 0.2 | 2.1 | 11.5 | 29.6 |
| Preparation D | 0.8 | 19.9 | 0.9 | 4.0 | 15.1 | 39.6 | 3.2 | 0.8 | 4.2 | 10.9 |
| Preparation E | ≤0.5 | 14.5 | ≤0.5 | 5.0 | 13.5 | 61.0 | 5.0 | ≤0.5 | ≤0.5 | <0.5 |
| Preparation F | 0.4 | 17.3 | 0.5 | 4.5 | 14.3 | 50 | 4.1 | 0.4 | 2.2 | 5.6 |

TABLE 8

Ratio between omega 6 fatty acids and omega 3 fatty acids on PS

|  | Omega 6/omega 3 ratio |
|---|---|
| Preparation A | 0.7 |
| Preparation A1 | 0.63 |
| Preparation A2 | 0.9 |
| Preparation B | ≤0.01 |
| Preparation C | 0.06 |
| Preparation D | 2.2 |
| Preparation E | ≥10 |
| Preparation F | 4.2 |

TABLE 9

Fatty acid content* and Source of Preparations G-N

|  | w/w %* LA conjugated to PS/w/w % DHA conjugated to PS | w/w % Linolenic acid conjugated to PS/w/w % DHA conjugated to PS | w/w % LA conjugated to PS/w/w % EPA conjugated to PS | w/w % Linolenic acid conjugated to PS/w/w % EPA conjugated to PS | % Soy PS Source | % Marine PS Source |
|---|---|---|---|---|---|---|
| Preparation G | 3:1 | 0.24:1 | 7.7:1 | 0.6:1 | 50 | 50 |
| Preparation H | 2.4:1 | 0.2:1 | 6.3:1 | 0.5:1 | 45 | 55 |
| Preparation I | 2:1 | 0.16:1 | 5:1 | 0.4:1 | 40 | 60 |
| Preparation J | 1.6:1 | 0.13:1 | 4.2:1 | 0.3:1 | 35 | 65 |
| Preparation K | 1.3:1 | 0.1:1 | 3.3:1 | 0.27:1 | 30 | 70 |
| Preparation L | 0.75:1 | 0.06 | 1.9:1 | 0.16:1 | 20 | 80 |
| Preparation M | 0.53:1 | 0.04:1 | 1.4:1 | 0.1:1 | 15 | 85 |
| Preparation N | 0.33:1 | 0.03:1 | 0.9:1 | 0.07:1 | 10 | 90 |

*Weight percent of a fatty acid conjugated to PS relative to weight of the total fatty acids conjugated to PS

The invention claimed is:

1. A preparation comprising a non-mammalian derived mixture of serine glycerophospholipid conjugates, wherein the mixture comprises (a) linoleic acid (C18:2) conjugated to phosphatidylserine (PS), (b) docosahexaenoic acid (DHA) conjugated to PS, and (f) eicosapentaenoic acid (EPA) conjugated to PS, in which mixture the w/w % of (a)/the w/w % of (b) is from about 0.09 to about 3.6 and the w/w % of (a)/w/w % of (f) is from about 0.23 to about 9.4.

2. A preparation according to claim 1, wherein the serine glycerophospholipid conjugates constitute at least 10% w/w of the preparation.

3. A preparation according to claim 2, wherein the serine glycerophospholipid conjugates constitute at least 20% w/w of the preparation.

4. A preparation according to claim 3, wherein the serine glycerophospholipid conjugates constitute at least 40% w/w of the preparation.

5. A preparation according to claim 4, wherein the serine glycerophospholipid conjugates constitute at least 50% w/w of the preparation.

6. A preparation according to claim 5, wherein the serine glycerophospholipid conjugates constitute at least 54% w/w of the preparation.

7. A preparation according to claim 1 further comprising (c) linolenic acid (C18:3) conjugated to PS, wherein the w/w % of (c)/w/w % of (b) is from about 0.01 to about 0.3.

8. A preparation according to claim 7, wherein the w/w % of (c)/w/w % of (f) is from about 0.02 to about 0.8.

9. A method of improving a condition in a subject suffering from a cognitive disease or disorder comprising administering to the subject an effective amount of a preparation according to claim 1, wherein the cognitive disease or disorder is selected from the group consisting of age-associated memory impairment and mild cognitive impairment.

10. A nutritional, pharmaceutical or nutraceutical composition, or a functional food comprising the preparation of claim 1.

11. A method for improving a condition in a subject suffering from a cognitive disease or disorder which comprises administering to the subject an effective amount of the nutritional, pharmaceutical or nutraceutical composition or the functional food of claim 10, wherein the cognitive disease or disorder is selected from the group consisting of age-associated memory impairment and mild cognitive impairment.

* * * * *